United States Patent
Ito et al.

(10) Patent No.: US 8,166,855 B2
(45) Date of Patent: May 1, 2012

(54) THIN SECTION PREPARING APPARATUS AND THIN SECTION PREPARING METHOD

(75) Inventors: Tetsumasa Ito, Chiba (JP); Koji Fujimoto, Chiba (JP)

(73) Assignee: Seiko Instruments Inc., Chiba (JP)

( * ) Notice: Subject to any disclaimer, the term of this patent is extended or adjusted under 35 U.S.C. 154(b) by 603 days.

(21) Appl. No.: 12/272,398

(22) Filed: Nov. 17, 2008

(65) Prior Publication Data

US 2009/0133556 A1  May 28, 2009

(30) Foreign Application Priority Data

Nov. 21, 2007 (JP) ................ 2007-302243

(51) Int. Cl.
*B26D 1/00* (2006.01)
*B26D 7/06* (2006.01)

(52) U.S. Cl. ................ 83/13; 83/109; 83/112

(58) Field of Classification Search ............. 83/155.1, 83/109, 112, 932, 915.5, 367, 111, 113, 15
See application file for complete search history.

(56) References Cited

U.S. PATENT DOCUMENTS

| | | | | |
|---|---|---|---|---|
| 4,681,002 A | * | 7/1987 | Nakaya | 83/76.1 |
| 5,713,255 A | * | 2/1998 | Izvozichikov et al. | 83/24 |
| 6,318,224 B1 | * | 11/2001 | Hoyland | 83/23 |
| 7,861,630 B2 | * | 1/2011 | Sorensen et al. | 83/42 |
| 2007/0157786 A1 | | 7/2007 | Miyatani et al. | |
| 2009/0165627 A1 | * | 7/2009 | Walter | 83/713 |
| 2010/0107836 A1 | * | 5/2010 | Lindee | 83/23 |

FOREIGN PATENT DOCUMENTS

JP    2007-178287 A    7/2007

* cited by examiner

*Primary Examiner* — Boyer D Ashley
*Assistant Examiner* — Omar Flores Sanchez
(74) *Attorney, Agent, or Firm* — Brinks Hofer Gilson & Lione (57) ABSTRACT

A thin section preparing apparatus prepares a thin section from an embedded block having a biological sample embedded and carries the thin section. The thin section preparing apparatus includes a cutter, an approaching and separating mechanism, a carrying mechanism, a moving unit, a sliding mechanism and a control unit. The cutter slices the block at a pull angle. The approaching and separating mechanism relatively moves the block and the cutter along an approaching and separating direction. The carrying mechanism having a carrying body is arranged as one end side is near a nose, and the moving unit moves the body along a transport direction. The sliding mechanism relatively moves the block and the body along a moving direction. The control unit controls a combined velocity vector that combines a transport velocity vector of the body along the transport direction with a travel velocity vector of the body along the moving direction to be nearly equal to a block velocity vector of the embedded block along the approaching and separating direction.

12 Claims, 10 Drawing Sheets

THIN SECTION PREPARING APPARATUS AND THIN SECTION PREPARING METHOD

REFERENCE TO THE RELATED APPLICATIONS

This application claims priority under 35 U.S.C. §119 to Japanese Patent Application No. JP2007-302243 filed on Nov. 21, 2007, the entire content of which is hereby incorporated by reference.

BACKGROUND OF THE INVENTION

1. Field of the Invention

The present invention relates to a thin section preparing apparatus and a thin section preparing method, in which an embedded block having a biological sample embedded therein is sliced to prepare a thin section and the prepared thin section is carried to a subsequent process step as a step before a thin section sample is prepared for use in physicochemical experiment or microscopic observation.

2. Description of the Related Art

Heretofore, as one method of examining a biological sample taken out of a human body or a laboratory animal, such a method is known that a biological sample is sliced in an ultrathin section and applied to various stains, and then examined by microscopic observation. This examination method is mainly known as a technique that is adopted in conducting a toxicological examination or a histopathological examination, which is one of examinations prior to clinical trials in new drug development.

Generally, in conducting this examination, in order to slice a biological sample so as not to damage the form of soft tissue or cells, first, the biological sample is embedded in an embedding material such as paraffin in advance to form an embedded block. Then, this embedded block is sliced to have a thickness of about 2 to 5 micrometers, whereby a thin section is prepared. In this manner, even though an examination subject is soft tissue, the examination subject can be sliced in an ultrathin section without damaging the form.

Then, after the thin section is carried, it is fixed on a substrate such as a slide glass, whereby a thin section sample can be prepared. Generally, an operator observes the thin section sample under a microscope to conduct various examinations. In microscopic observation, because a wrinkle or a breakage in a thin section hampers observation, the preparation of a thin section with no wrinkle or breakage is demanded.

For example, in preclinical trials, an enormous number of thin sections prepared from hundreds of embedded blocks are sometimes used. On this account, an operator requires a huge number of man-hours to prepare thin sections. In order to reduce even a small amount of these man-hours, an attempt is made to automate a sequence of process steps of preparing a thin section to continuously prepare thin sections.

Particularly, in order to automatically and continuously slice an embedded block, it is necessary to automatically carry thin sections sliced by a cutter. To this end, for example, in a thin section preparing apparatus described in, for instance, JP-A-2007-178287, an endless belt is used as a carrying mechanism. This endless belt is wound between a roller arranged near a cutter along the nose direction almost in parallel with the nose of the cutter and a plurality of the other rollers arranged on the rear side of the roller, and the endless belt is configured to travel in the transport direction nearly vertical to the nose direction seen in plane.

According to this thin section preparing apparatus, while a thin section is being sliced off from an embedded block by the cutter, the sliced thin section can be passed onto the endless belt arranged near the cutter. Therefore, the embedded block is sliced by the cutter while the endless belt is traveling in the transport direction, whereby thin sections can be automatically carried to the subsequent process step as thin sections are prepared. As described above, since the prepared thin sections can be automatically carried, working efficiency can be improved. Thus, man-hours to be consumed in preparing thin sections can be reduced.

When the embedded block is repeatedly sliced by a cutter, the sharpness of the cutter is gradually degraded. In order to maintain the sharpness of the cutter as long as possible, such a method is generally known that a pull angle is provided to a cutter with respect to an embedded block for slicing. In addition, the provision of the pull angle to the cutter with respect to the embedded block means that the cutter is arranged in such a way that the nose direction intersects at an angle other than an angle vertical to an approaching and separating direction seen in plane in which the cutter and the embedded block approach and separate from each other for slicing the embedded block.

Therefore, preferably, the pull angle is provided to the cutter also in the apparatus before. However, it is necessary to carry sliced thin sections with the use of the endless belt, which might cause inconvenience. In other words, in passing a thin section onto the endless belt, a wrinkle or a breakage might occur in the thin section. The detail will be described below.

Figure 11:
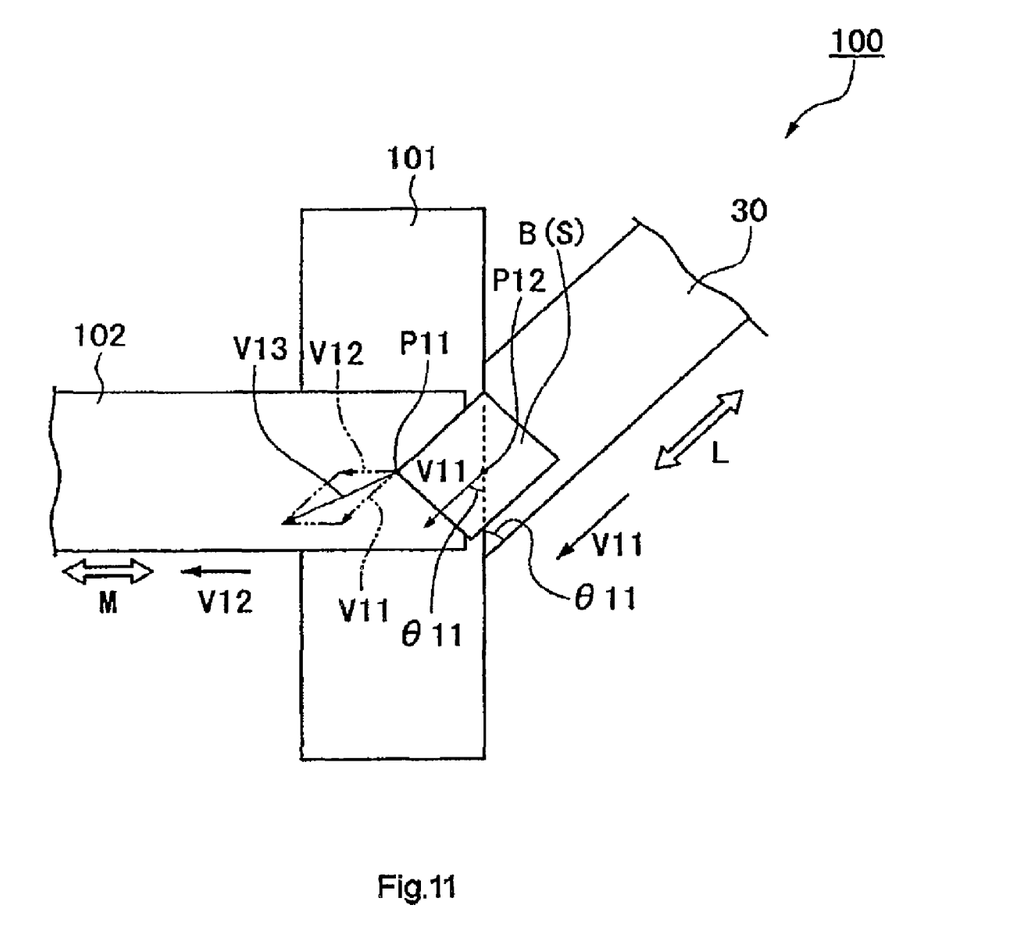
FIG. 11 shows a top view depicting a thin section preparing apparatus before in slicing an embedded block, showing a diagram illustrative of a current problem.

As shown in FIG. 11, in slicing off a thin section S from an embedded block B, the rate of travel is different between a portion P11 that has been sliced off by a cutter and placed on an endless belt 102 and a portion P12 that is not sliced off yet and remains in the embedded block B.

In other words, to the portion P11 placed on the endless belt 102, a block velocity vector V11 in approaching the cutter 101 and the embedded block B to each other along an approaching and separating direction L and a transport velocity vector V12 in moving the endless belt 102 along a transport direction M are applied. Thus, the rate of travel of the portion P11 placed on the endless belt 102 is a combined velocity vector V13 that is the combined vector of the block velocity vector V11 with the transport velocity vector V12. On the other hand, the rate of travel of the portion P12 remaining in the embedded block B is the block velocity vector V11 that is the rate of travel of the embedded block B.

Therefore, in order to automatically prepare the thin section S in the apparatus before, the portion P11 placed on the endless belt 102 and the portion P12 remaining in the embedded block B are being moved at different rates of travel (at the combined velocity vector V13 and at the block velocity vector V11) in a single thin section S. On this account, because a difference is caused between the rates of travel in a single thin section S, a wrinkle or a breakage occurs in the thin section S.

SUMMARY OF THE INVENTION

The invention has been made in the light of the circumstances. An object is to provide a thin section preparing apparatus and a thin section preparing method, in which a cutter provided with a pull angle is used to automate the preparation of a thin section and the transport to the subsequent process step with no wrinkle or breakage in a thin section.

In order to solve the problems, the invention proposes the following schemes.

The invention is a thin section preparing apparatus that slices an embedded block having a biological sample embedded therein to prepare a thin section, and carries the thin section to a subsequent process step, the apparatus including: a cutter that slices the embedded block at a predetermined pull angle; an approaching and separating mechanism that relatively moves the embedded block and the cutter along an approaching and separating direction in which the embedded block and the cutter approach and separate from each other, and slices off the thin section from the embedded block; a carrying mechanism that has: a carrying body that is arranged as one end side thereof is near a nose of the cutter and the sliced thin section is placed on a top surface thereof; and a moving unit that moves the carrying body in a transport direction nearly vertical to a nose direction almost in parallel with the nose seen in plane, wherein the placed thin section is carried from one end side of the carrying body toward the other end side thereof along the transport direction; a sliding mechanism that relatively moves the embedded block and the carrying body along a moving direction; and a control unit that controls rates of travel of the sliding mechanism and the moving unit in slicing off the thin section from the embedded block in such a way that a combined velocity vector that combines a transport velocity vector of the carrying body along the transport direction with a relative travel velocity vector of the embedded block to the carrying body along the moving direction becomes nearly equal to a block velocity vector of the embedded block with respect to the cutter along the approaching and separating direction.

In addition, the invention is a thin section preparing method of slicing an embedded block having a biological sample embedded therein by a cutter to prepare a thin section and carrying the thin section to a subsequent process step, the method including the steps of: cutting wherein the embedded block and the cutter are relatively moved along an approaching and separating direction in which the embedded block and the cutter approach and separate from each other, and the thin section is sliced off from the embedded block at a predetermined pull angle; and carrying wherein the thin section sliced in the cutting step is placed on a top surface of a carrying body that is arranged as one end side thereof is near a nose of the cutter and is moved in a transport direction in which nearly vertical to a nose direction almost in parallel with the nose seen in plane, and the thin section is carried from one end side of the carrying body toward the other end side thereof along the transport direction, wherein in conducting the cutting step and the carrying step, control is conducted in such a way that the embedded block and the carrying body are relatively moved at a predetermined rate of travel along a moving direction, the carrying body is moved at a predetermined transport velocity, and a combined velocity vector that combines a relative travel velocity vector of the embedded block to the carrying body with a transport velocity vector of the carrying body becomes nearly equal to a block velocity vector of the embedded block with respect to the cutter along the approaching and separating direction.

In accordance with the thin section preparing apparatus and the thin section preparing method according to the invention, in the cutting step, the approaching and separating mechanism relatively moves the embedded block and the cutter along the approaching and separating direction in which the embedded block and the cutter approach and separate from each other, whereby the thin section can be sliced off from the embedded block by the cutter. On this occasion, because the cutter is provided with a predetermined pull angle, thin sections can be prepared while the sharpness of the cutter is maintained for a long time.

The thin section sliced in the cutting step is placed as one end side thereof is near the nose of the cutter, and turned on the top surface of the carrying body moving along the transport direction nearly in parallel to the nose direction which is also almost in parallel with the nose seen in plane. In other words, because the carrying body is arranged as one end side thereof is near the nose of the cutter, the embedded block and the cutter are relatively moved to automatically place the sliced thin section onto the top surface of the carrying body by the cutter. Since the carrying body is moved in the transport direction by the moving unit, the thin section placed the top surface can be carried from one end side of the carrying body toward the other end side thereof. Thus, since the thin section can be automatically carried to the subsequent process step, thin sections can be continuously prepared in the cutting step.

Particularly, in conducting the cutting step and in conducting the carrying step, the control unit controls the relative rate of travel of the embedded block and the carrying body by the sliding mechanism and the transport velocity of the carrying body by the moving unit as the following manner.

In other words, the combined velocity vector that combines the relative travel velocity vector of the embedded block to the carrying body along the nose direction with the transport velocity vector of the carrying body along the transport direction is controlled to be nearly equal to the block velocity vector of the embedded block with respect to the cutter along the approaching and separating direction. Therefore, the same block velocity vector acts on a portion of the thin section that has been sliced off from the embedded block by the cutter and already turned on the top surface of the carrying body and a portion of the thin section that is not sliced off yet by the cutter and remains on the embedded block side (the portion is connected to the embedded block).

Heretofore, different velocity vectors act on the thin section having been sliced by the cutter and the thin section remaining on the embedded block side. On this account, forces in different directions can act on the thin section during the thin section being fully sliced off, and a wrinkle or a breakage tends to occur. However, according to the invention, as described above, because no difference is caused in the rate of travel between the portion already sliced and the portion not sliced yet in a single thin section, no wrinkle or breakage occurs in the thin section. Accordingly, the thin section can be passed onto the carrying body with no wrinkle or breakage. Consequently, a thin section of high quality can be carried, and passed to the subsequent process step.

In addition, in the thin section preparing apparatus according to the invention, preferably, the carrying body contains a certain amount of a predetermined fluid.

In addition, in the thin section preparing method according to the invention, preferably, the carrying body contains a certain amount of a predetermined fluid, and in conducting the carrying step, surface tension of the fluid is used to carry the thin section while the thin section is brought into intimate contact with the carrying body.

In accordance with the thin section preparing apparatus and the thin section preparing method according to the invention, in conducting the carrying step, the carrying body containing a certain amount of a predetermined fluid is used, and the thin section is carried while the thin section is brought into intimate contact with the carrying body by surface tension. Thus, the position of the thin section is not shifted on the carrying body, and the thin section does not drop off from the carrying body. Accordingly, the thin section can be reliably carried to the subsequent process step.

In addition, in the thin section preparing apparatus according to the invention, preferably, the apparatus includes a charging mechanism that charges electric charges of polarities different from each other to the embedded block and to the carrying body.

In addition, in the thin section preparing method according to the invention, preferably, in conducting the carrying step, the thin section is carried while the thin section is brought into intimate contact with the carrying body by static electricity.

In accordance with the thin section preparing apparatus and the thin section preparing method according to the invention, the charging mechanism charges electric charges of polarities different from each other to the embedded block and to the carrying body in advance. Thus, in conducting the carrying step, the thin section can be carried while the thin section is brought into intimate contact with the carrying body by static electricity. On this account, the position of the thin section is not shifted on the carrying body, and the thin section does not drop off from the carrying body. Accordingly, the thin section can be reliably carried to the subsequent process step.

In addition, in the thin section preparing apparatus according to the invention, preferably, the carrying body is an endless belt.

In addition, in the thin section preparing method according to the invention, preferably, an endless belt is used as the carrying body.

In accordance with the thin section preparing apparatus and the thin section preparing method according to the invention, because a typical endless belt is used to configure the carrying body, the configuration can be simplified. Particularly, since the endless belt is rotated to continuously carry thin sections without interruption, the prepared thin sections can be carried more efficiently.

In addition, in the thin section preparing apparatus according to the invention, preferably, the approaching and separating mechanism has a guide rail extended along the approaching and separating direction and a stage movable along the guide rail as the stage holds the embedded block, and the sliding mechanism has a slider unit that moves the carrying body along the moving direction.

In addition, in the thin section preparing method according to the invention, preferably, in conducting the cutting step, the embedded block is moved along the approaching and separating direction, and the carrying body is moved along the nose direction.

In accordance with the thin section preparing apparatus and the thin section preparing method according to the invention, both of the embedded block and the cutter are not moved, the stage that holds the embedded block is simply moved along the guide rail, whereby the cutter and the embedded block can be relatively moved along the approaching and separating direction. Similarly, both of the embedded block and the carrying body are not moved, the carrying body is simply moved by the slider unit, whereby the embedded block and the carrying body can be relatively moved in the moving direction. Accordingly, such a complicated motion is unnecessary that the embedded block, the cutter and the carrying body are moved in different directions, and such a simple motion is enough that only the embedded block and the carrying body are moved in one directions. Therefore, the motions of the approaching and separating mechanism and the sliding mechanism can be simplified.

In addition, in the thin section preparing apparatus according to the invention, preferably, the approaching and separating mechanism fixes the embedded block in such a way that a side surface of the embedded block faces the nose of the cutter.

In addition, in the thin section preparing method according to the invention, preferably, in conducting the cutting step, the embedded block and the cutter are relatively moved in such a way that a side surface of the embedded block faces the nose of the cutter.

In accordance with the thin section preparing apparatus and the thin section preparing method according to the invention, in conducting the cutting step, the embedded block and the cutter are relatively moved while the approaching and separating mechanism fixes the embedded block in such a way that the side surface of the embedded block faces the nose of the cutter. Accordingly, when the embedded block is a rectangular parallelepiped, a sliced thin section is placed in parallel with the top surface of the carrying body along the transport direction. Thus, the thin section being carried can be easily handled in the subsequent process step. For example, because the thin section is being carried as it is in parallel with the carrying body, in fixing the thin section onto the substrate such as a slide glass in the subsequent process step, positioning can be conducted easily.

In accordance with the thin section preparing apparatus and the method of preparing a thin section according to the invention, a cutter provided with a pull angle is used to automate the preparation of a thin section and the transport to the subsequent process step with no wrinkle or breakage in a thin section.

BRIEF DESCRIPTION OF THE DRAWINGS

The teachings of the invention can be readily understood by considering the following detailed description in conjunction with the accompanying drawings, in which.

DETAILED DESCRIPTION OF THE INVENTION

First Embodiment

Hereinafter, a first embodiment according to the invention will be described with reference to FIGS. 1 to 7.

Figure 1:
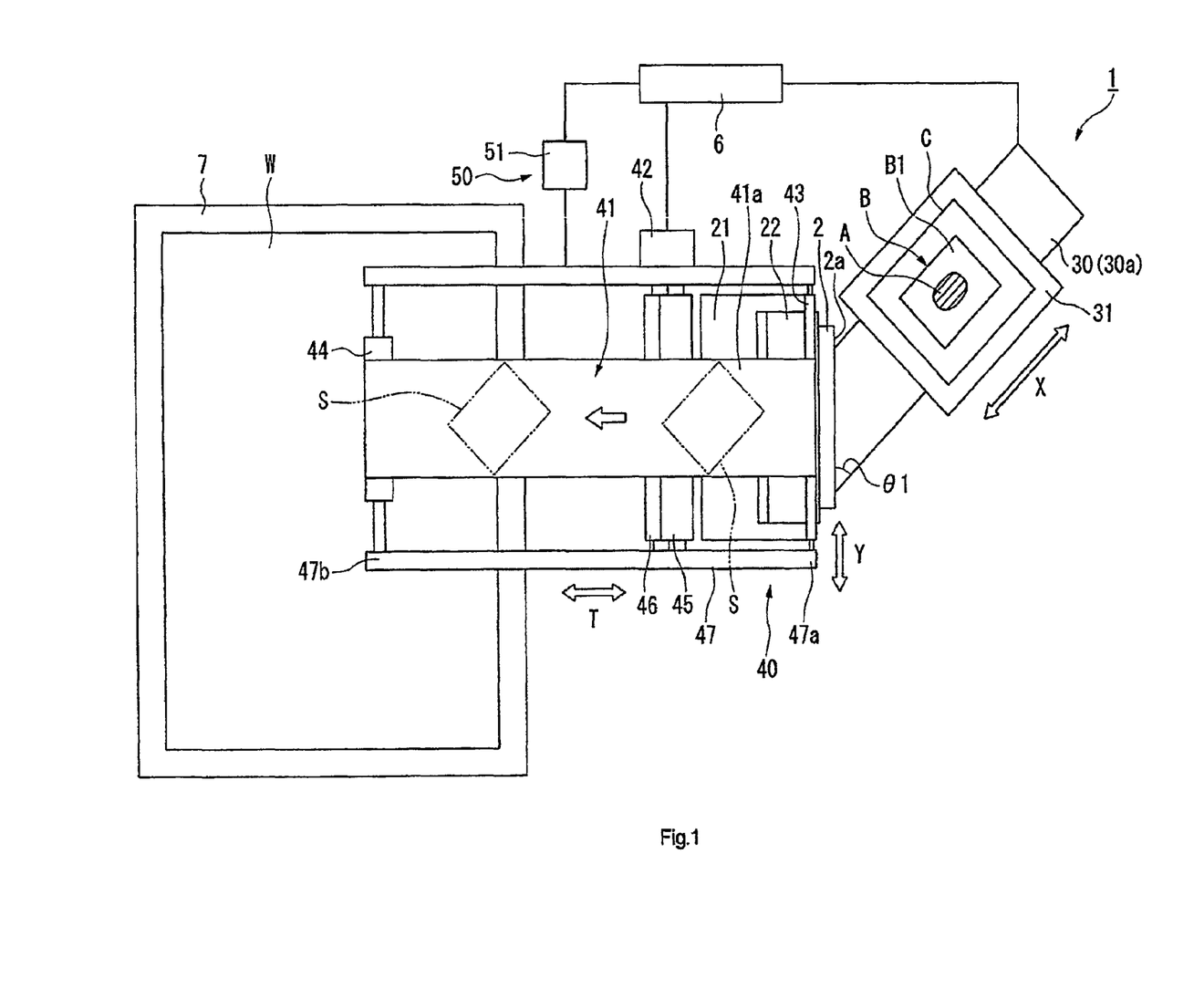
FIG. 1 shows a top view depicting a thin section preparing apparatus according to a first embodiment of the invention.

As shown in FIG. 1, a thin section preparing apparatus 1 according to the embodiment is an apparatus that slices an embedded block B in a nearly rectangular parallelepiped having a biological sample A embedded therein in an ultrathin section having a thickness of about 3 to 5 micrometers to prepare a thin section S and carries the prepared thin section S to a subsequent process step. In addition, this thin section preparing apparatus 1 is mainly used in the process of examining and observing the biological sample A included in the thin section S.

For example, the biological sample A is tissue such as an organ taken out of a human body or a laboratory animal, which is freely selected in the fields of medical cares, drugs, foods, and biology. In addition, the embedded block B is a block that the biological sample A is embedded in an embedding agent B1, that is, the biological sample A is covered and solidified with the embedding agent B1. More specifically, such an embedded block B is prepared as the following manner. First, a block of the biological sample A is immersed in formalin to solidify protein configuring the biological sample A. Then, tissue is formed into a solid state, and then cut into blocks in proper size. Lastly, the moisture inside the cut biological sample A is replaced with the embedding agent B1, and then the cut biological sample A is placed in the dissolved embedding agent B1 for solidification to prepare an embedded block B. Here, the embedding agent B1 is a material that is easily liquefied, cooled and solidified and is immersed in ethanol for dissolution, which is a resin or paraffin, for example. Hereinafter, the configuration of the thin section preparing apparatus 1 will be described.

Figure 2:
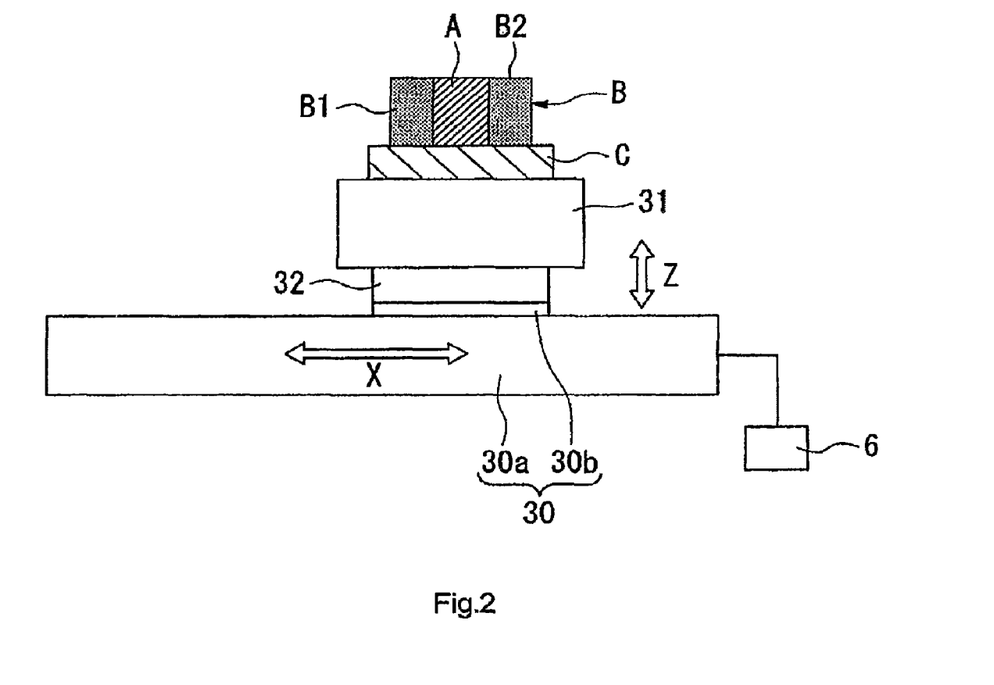
FIG. 2 shows a side view depicting an X-stage of the thin section preparing apparatus shown in FIG. 1.
Figure 3:
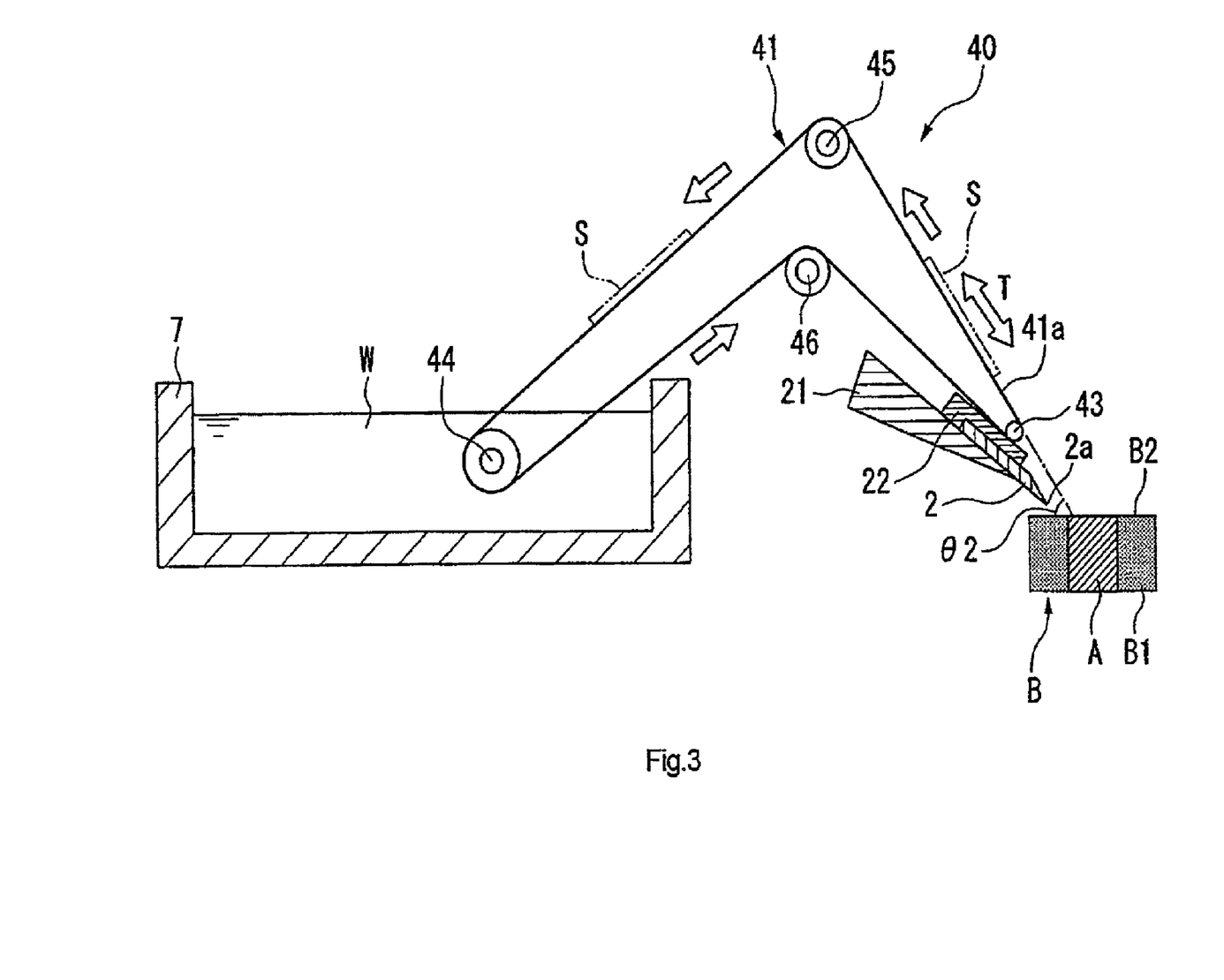
FIG. 3 shows a side view depicting a cutter, a carrying mechanism and a liquid bath of the thin section preparing apparatus shown in FIG. 1.

As shown in FIGS. 1 to 3, the thin section preparing apparatus 1 has a cutter 2 that slices an embedded block B at a predetermined pull angle θ1; an X-stage (approaching and separating mechanism) 30 that relatively moves the embedded block B and the cutter 2 along an approaching and separating direction X in which they approach and separate from each other and slices off a thin section S from the embedded block B; a carrying mechanism 40 that has: an endless belt (carrying body) 41 that is arranged as one end side thereof is near a nose 2a of the cutter 2 and the sliced thin section S is placed on a top surface 41a; a motor (moving unit) 42 that moves the endless belt 41 along a transport direction T nearly in parallel to a nose direction N almost in parallel with the nose 2a seen in plane (see FIG. 4), in which the placed thin section S is carried from one end side of the endless belt 41 toward the other end side thereof; a sliding mechanism 50 that relatively moves the embedded block B and the endless belt 41 along a moving direction Y (see FIG. 4); and a control unit 6 that controls the X-stage 30, the carrying mechanism 40, and the sliding mechanism 50 to operate as described later.

As shown in FIG. 1, the cutter 2 is arranged above a guide rail 30a of the X-stage 30, described later. In addition, as shown in FIG. 3, the cutter 2 is clamped from the upper and lower surfaces by a platform 21 and a holder 22. The platform 21 is arranged along the moving direction Y so as to support the cutter 2 and the holder 22 on the top surface thereof, and is supported by a support member, not shown. The holder 22 is arranged as a part thereof is abutted against the top surface of the platform 21. Thus, the cutter 2 is held as the nose 2a is exposed with no wobbles. In addition, the holder 22 is configured that it is removed from the platform 21, and the cutter 2 can be changed.

As shown in FIG. 2, the X-stage 30 has the guide rail 30a that is extended along the approaching and separating direction X, and a stage 30b that is movable along the guide rail 30a as the stage 30b supports a sample stage 31 that holds the embedded block B.

In other words, in the embodiment, both of the embedded block B and the cutter 2 are not moved, the stage 30b supporting the sample stage 31 that holds the embedded block B is simply moved along the guide rail 30a, whereby the cutter 2 and the embedded block B can be relatively moved along the approaching and separating direction X. In addition, the operation of the X-stage 30 is controlled by the control unit 6. This operation will be described later.

In addition, as shown in FIG. 2, the following components are arranged on the stage 30b of the X-stage 30: the sample stage 31 that positions and fixes a cassette C having the embedded block B placed thereon, and a Z-stage 32 that moves the sample stage 31 along a vertical direction Z to adjust the height of the embedded block B, in which they are overlapped with each other. In addition, as similar to the X-stage 30, the operation of the Z-stage 32 is controlled by the control unit 6. More specifically, the Z-stage 32 is controlled so as to ascend the embedded block B by a predetermined amount as matched with the slide motion of the stage 30b. Thus, the embedded block B is cut in a predetermined thickness, and a thin section S is sliced off.

As shown in FIGS. 1 and 3, the carrying mechanism 40 has a front roller 43 that is arranged as close to the nose 2a, a rear roller 44 that is arranged on the rear side of the cutter 2, an endless belt 41 that is wounded between the front roller 43 and the rear roller 44, a motor 42 that moves the endless belt 41 along the transport direction T, and a frame 47 that rotatably retains the shafts of the rollers 43 and 44.

As shown in FIG. 1, both of the front roller 43 and the rear roller 44 are arranged almost in parallel with the moving direction Y. As shown in FIG. 3, in the rollers 43 and 44, the front roller 43 is retained by the shaft on front end portions 47a of the frame 47 as a clearance is spaced to pass the endless belt 41 between the front roller 43 and the holder 22 of the cutter 2. On the other hand, as shown in FIG. 1, the rear roller 44 is rotatably retained by the shaft on rear end portions 47b of the frame 47 as the rear roller 44 is immersed in a fluid W in a liquid bath 7, described later, together with the frame 47. As shown in FIG. 3, between the front roller 43 and the rear roller 44, two intermediate rollers 45 and 46 are rotatably retained by the shafts on the frame 47 and located above the front roller 43 and the rear roller 44. These two intermediate rollers 45 and 46 are arranged between the front roller 43 and the rear roller 44 almost in parallel with the moving direction Y.

As shown in FIG. 3, the endless belt 41 is wounded on the intermediate rollers 45 and 46 between the front roller 43 and the rear roller 44 so as to abut against the upper parts of the intermediate rollers 45 and 46. Particularly, because the endless belt 41 is immersed in the fluid W in the liquid bath 7 near the rear roller 44, the endless belt 41 is simply moved by the motor 42 to contain a certain amount of the fluid W. In addition, the intermediate rollers 45 and 46 against which the endless belt 41 abuts are located above more than the front roller 43. In addition, the transport direction T in the embodiment is angled at a transport angle θ2 with respect to a front surface B2 of the embedded block B, the transport angle θ2 being an angle formed of a plane in parallel with the front surface B2 of the embedded block B intersecting with a plane in parallel with the top surface 41a of the endless belt 41.

As shown in FIG. 1, the motor 42 is connected to the intermediate roller 46. The motor 42 is driven to run the endless belt 41 of the carrying mechanism 40 endlessly in the transport direction T to carry the placed thin section S from one end side of the endless belt 41 toward the other end side thereof. In addition, the operation of the motor 42 is controlled by the control unit 6 as similar to the X-stage 30. This operation will be described later.

As shown in FIG. 1, the frame 47 is a pair of frames that is arranged in parallel so as to retain both ends of the shafts of the rollers 43 to 46, and is extended along the transport direction T. In addition, in FIG. 3, the frame 47 is omitted in the drawing. The frame 47 is supported by a cabinet, not shown.

As shown in FIG. 1, the sliding mechanism 50 has a slider unit 51 that moves the individual rollers 43 to 46 wounded with the endless belt 41 along the moving direction Y through the frame 47. For example, for the slider unit 51, such a mechanism can be named in which a cabinet, not shown, that supports the frame 47 and a stage, not shown, that supports the cabinet are provided and the stage is moved by a servo motor. Therefore, the slider unit 51 is operated to move the endless belt 41 in the moving direction Y together with the frame 47.

In other words, in the embodiment, both of the embedded block B and the endless belt 41 are not moved, the individual rollers 43 to 46 wounded with the endless belt 41 are simply moved by the slider unit 51 through the frame 47, whereby the endless belt 41 and the embedded block B can be relatively moved along the moving direction Y. In addition, the operation of the slider unit 51 is controlled by the control unit 6 as similar to the X-stage 30 and the motor 42. This operation will be described later.

For example, the liquid bath 7 stores therein the fluid W such as water, hot water or a specific solution. In addition, the liquid bath 7 is designed long enough in the moving direction Y so as not to interfere when the endless belt 41 is moved along the moving direction Y by the sliding mechanism 50.

Figure 4:
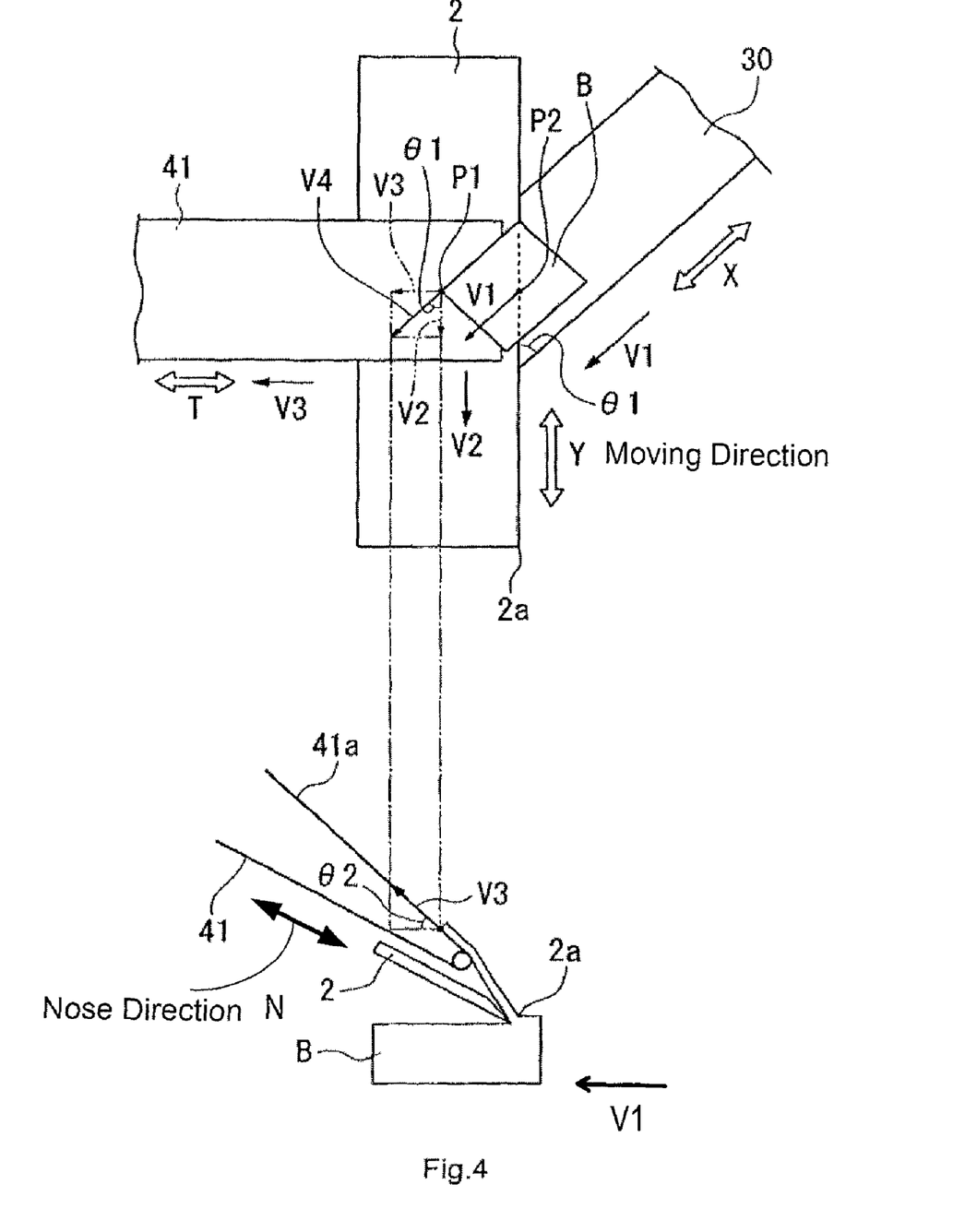
FIG. 4 shows a top view and a side view depicting an embedded block being sliced in the thin section preparing apparatus shown in FIG. 1, showing diagrams illustrative of the function of a control unit.

As shown in FIG. 4, the control unit 6 allows the cutter 2 to slice off a thin section S while the X-stage 30 relatively brings the embedded block B close to the cutter 2 at a block velocity vector V1 along the approaching and separating direction X. On this occasion, the control unit 6 controls a relative travel velocity vector V2 of the embedded block B to the endless belt 41 along the moving direction Y by the sliding mechanism 50 and a transport velocity vector V3 of the endless belt 41 along the transport direction T by the motor 42 as below. In other words, as shown in FIG. 4, the control unit 6 controls a combined velocity vector V4 that combines the travel velocity vector V2 with the transport velocity vector V3 to be nearly equal to the block velocity vector V1. More specifically, the control unit 6 controls the rates of the travel velocity vector V2 and the transport velocity vector V3 as follows with the pull angle $\theta 1$ and the transport angle $\theta 2$:

$|V2|=|V1|\cos \theta 1,$ $|V3|=|V1|\sin \theta 1/\cos \theta 2.$

Figure 5:
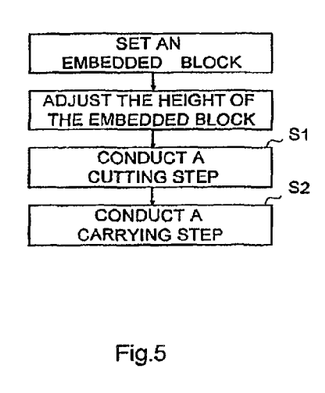
FIG. 5 shows a flow chart depicting a thin section preparing method according to a first embodiment of the invention.

Next, a method of preparing the thin section S using the thin section preparing apparatus 1 according to the embodiment will be described. FIG. 5 shows a flow chart depicting a method of preparing the thin section S according to the invention.

First, the cassette C on which the embedded block B is placed is set on the sample stage 31 in a predetermined orientation. Subsequently, the height of the embedded block B is adjusted by the Z-stage 32 through the sample stage 31. For example, the height to be adjusted is preferably the height that the embedded block B can be sliced in a predetermined thickness (about 3 to 5 micrometers) by the cutter 2.

Figure 6:
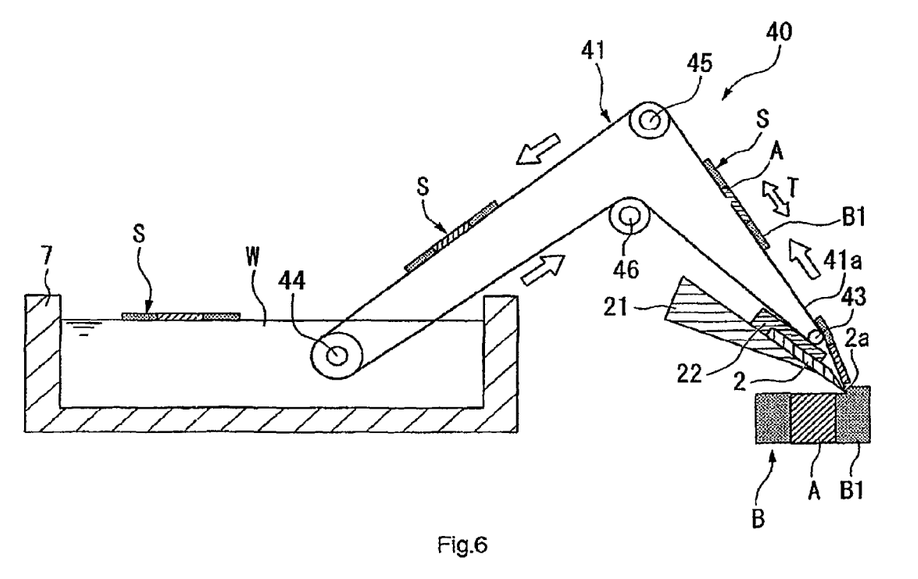
FIG. 6 shows a side view depicting the cutter, the carrying mechanism and the liquid bath of the thin section preparing apparatus shown in FIG. 1 in preparing thin sections.
Figure 7:
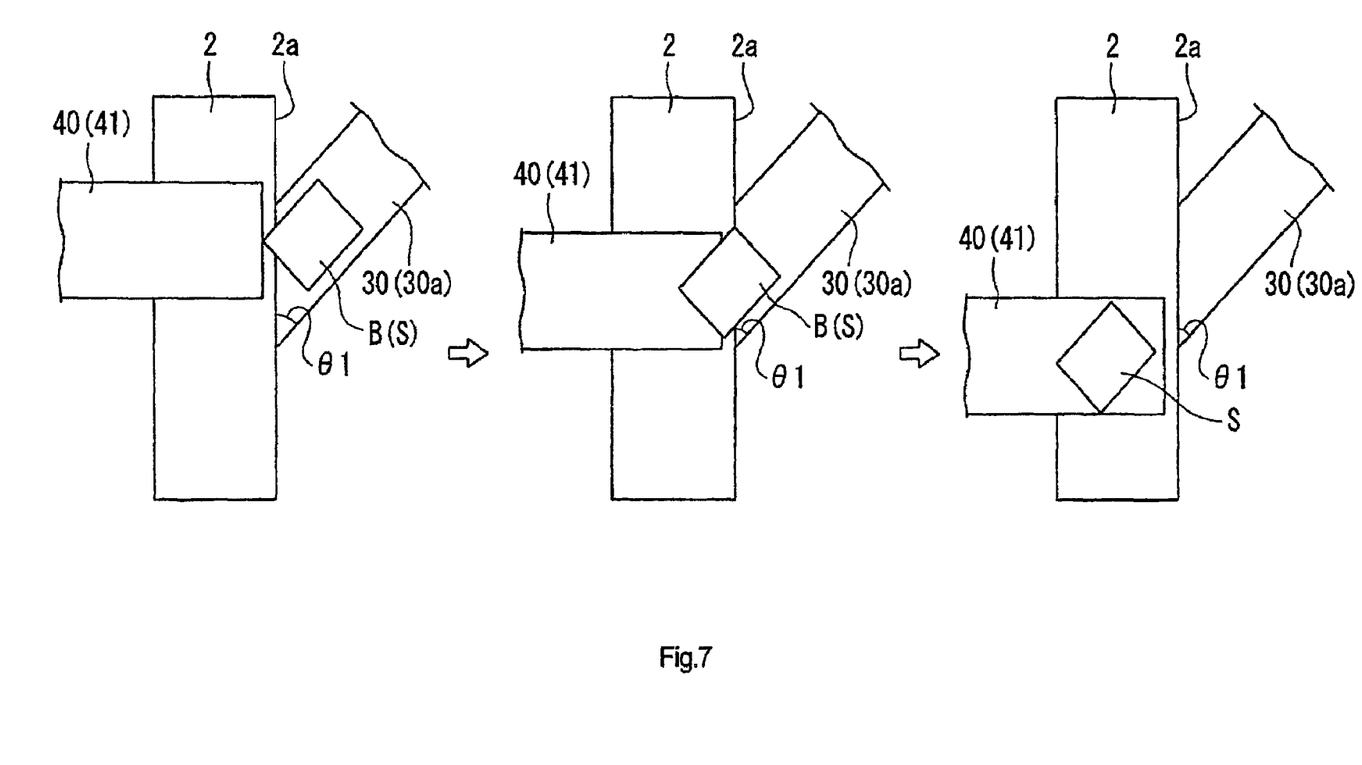
FIG. 7 shows top views depicting the thin section preparing apparatus shown in FIG. 1 in preparing thin sections.

After the adjustment of the height of the embedded block B is finished, a cutting step S1 in which the embedded block B is cut to slice off the thin section S and a carrying step S2 in which the sliced thin section S is carried to the liquid bath 7 are continuously conducted. In other words, as shown in FIGS. 6 and 7, first, the stage 30b is moved along the guide rail 30a in such a way that the embedded block B and the cutter 2 are brought into intimate contact with each other. Thus, the cutter 2 can slice off a thin section S from the embedded block B. On this occasion, because the cutter 2 is provided with a predetermined pull angle $\theta 1$, the thin section S can be prepared while the sharpness of the cutter 2 can be maintained for a long time.

On the other hand, the motor 42 is driven to run the endless belt 41 while the sliding mechanism 50 moves the endless belt 41 in the moving direction Y at the same time at which the stage 30b is operated. Thus, the thin section S that is being gradually sliced off by the cutter 2 is turned above the cutter 2, passed over the front roller 43, and begins to be placed onto the top surface 41a of the endless belt 41. In other words, because the endless belt 41 is arranged as one end side of the endless belt 41 is near the nose 2a of the cutter 2, the embedded block B and the cutter 2 are relatively moved to automatically place the sliced thin section S on the top surface 41a of the endless belt 41 by the cutter 2. The thin section S is fully sliced off from the embedded block B, carried on the rear side of the cutter 2 as the thin section S is placed on the top surface 41a of the endless belt 41, and then advanced toward the rear roller 44. Then, the thin section S carried to the liquid bath 7 together with the endless belt 41 leaves the endless belt 41 at the time at which the thin section S is contacted with the fluid W stored in the liquid bath 7. Then, the thin section S is floated and extended on the fluid W. After that, the thin section S is passed to the subsequent process step. As described above, since the thin sections S can be automatically carried to the subsequent process step, the thin sections S can be continuously prepared in the cutting step S1.

Particularly, in conducting the process steps above, the control unit 6 controls the combined velocity vector V4 that combines the travel velocity vector V2 with the transport velocity vector V3 to be nearly equal to the block velocity vector V1. Therefore, the same block velocity vector V1 acts on a portion P1 of the thin section S, which has been sliced off from the embedded block B by the cutter 2 and already placed onto the top surface 41a of the endless belt 41, and on a portion P2 of the thin section S, which is not sliced off yet by the cutter 2 and still remains on the embedded block B side (the portion P2 is connected to the embedded block B).

Heretofore, different velocity vectors act on the thin section S already sliced by the cutter 2 and on the thin section S remaining on the embedded block B side. On this account, forces in different directions can act on the thin section S during the thin section S being fully sliced off, and a wrinkle or a breakage tends to occur. However, according to the invention, as described above, because no difference is caused in the rate of travel between the portion P1 already sliced and the portion P2 not sliced off yet in a single thin section S, no wrinkle or breakage occurs in the thin section S. Accordingly, the thin section S can be passed onto the endless belt 41 with no wrinkle or breakage. Consequently, a thin section S of high quality can be carried, and passed to the subsequent process step.

In addition, in the cutting step S1, the sample stage 31 on which the embedded block B is fixed is simply moved along the guide rail 30a of the X-stage 30, whereby the embedded block B and the cutter 2 can be relatively moved along the approaching and separating direction X. In addition, the frame 47 that supports the individual rollers 43 to 46 wounded with the endless belt 41 is simply moved by the slider unit 51 along the moving direction Y, whereby the embedded block B and the endless belt 41 can be relatively moved along the moving direction Y. Accordingly, such a complicated motion is unnecessary that the embedded block B, the cutter 2 and the endless belt 41 are moved in different directions, and such a simple motion is enough that the embedded block B and the endless belt 41 are simply moved in one directions. Thus, the motions of the X-stage 30 and the sliding mechanism 50 can be simplified.

In addition, in the carrying step S2, because a typical endless belt 41 is used to configure the carrying body, the configuration can be simplified. Particularly, since the endless belt 41 is rotated by the motor 42 to continuously carry thin sections S without interruption, the prepared thin sections S can be carried more efficiently.

In addition, in the carrying step S2, the endless belt 41 containing a certain amount of a predetermined fluid is used as the endless belt 41, and the thin sections S is carried while the thin section S and the endless belt 41 are brought into intimate contact with each other by surface tension. Thus, the position of the thin section S is not shifted on the endless belt 41, and the thin section S does not drop off from the endless belt 41. Accordingly, the thin section S can be reliably carried to the subsequent process step.

Second Embodiment

Figure 8:
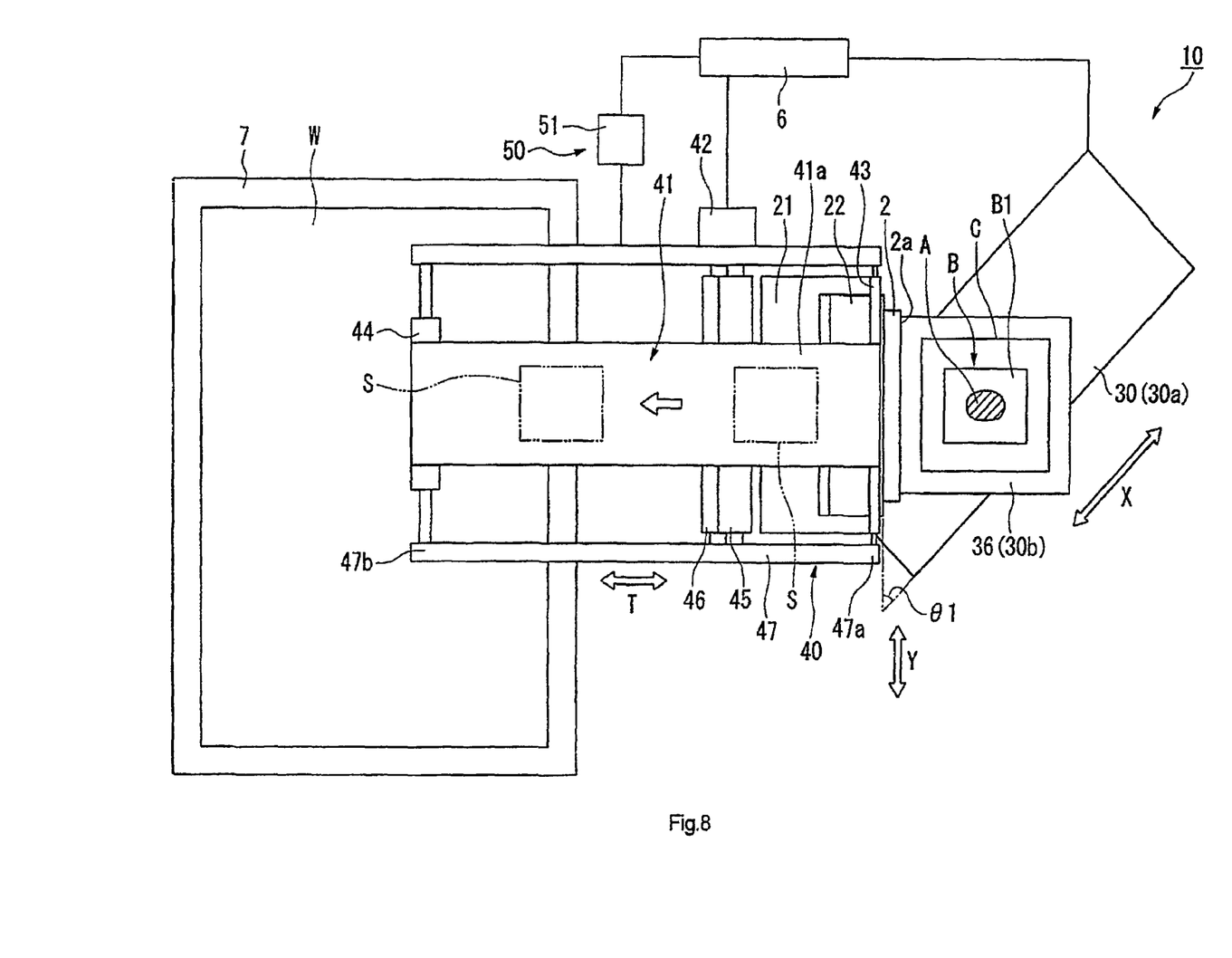
FIG. 8 shows a top view depicting a thin section preparing apparatus according to a second embodiment of the invention.
Figure 9:
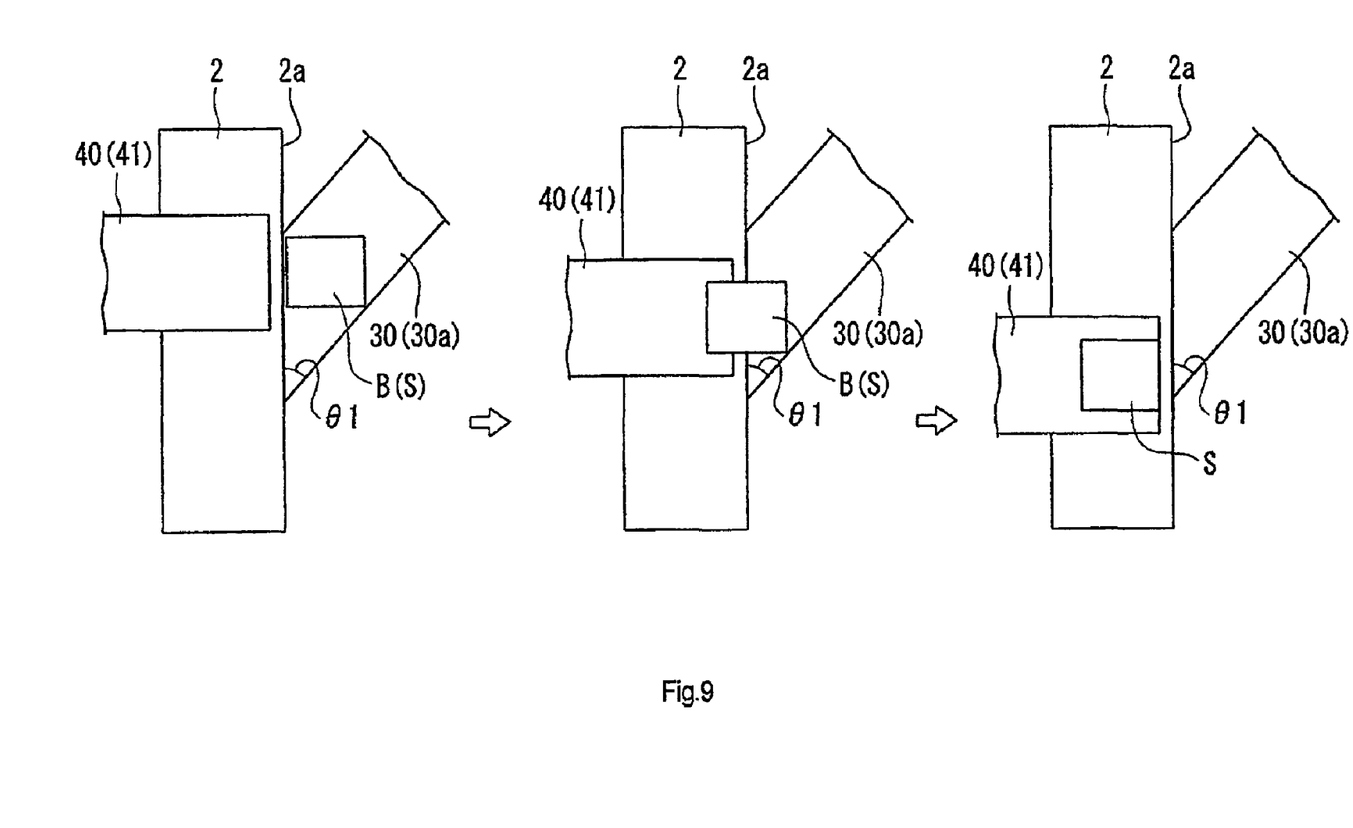
FIG. 9 shows top views depicting the thin section preparing apparatus shown in FIG. 8 in preparing thin sections.

Next, a second embodiment of the invention will be described with reference to FIGS. 8 and 9. In addition, in the second embodiment, the same components as those in the first embodiment are designated the same numerals and signs for omitting the descriptions.

The point different between the second embodiment and the first embodiment is the direction in which an embedded block B is fixed.

In other words, according to a thin section preparing apparatus 10, in conducting the cutting step S1, an embedded block B and a cutter 2 are relatively moved by an X-stage 30 while the embedded block B is fixed on a sample stage 36 in such a way that the side surface of the embedded block B faces a nose 2a of the cutter 2. Therefore, a sliced thin section S is placed in parallel on a top surface 41a of an endless belt 41 along the transport direction T. Thus, the thin section S being carried can be easily handled in the subsequent process step. For example, because the thin section is carried as it is in parallel with the endless belt 41, the thin section S can be easily positioned in fixing it to a substrate such as a slide glass in the subsequent process step.

As discussed above, the embodiments of the invention have been described in detail with reference to the drawings. However, the specific configurations will not be limited to the embodiments above, and design modifications can be included within the scope not deviating from the teachings of the invention.

Figure 10:
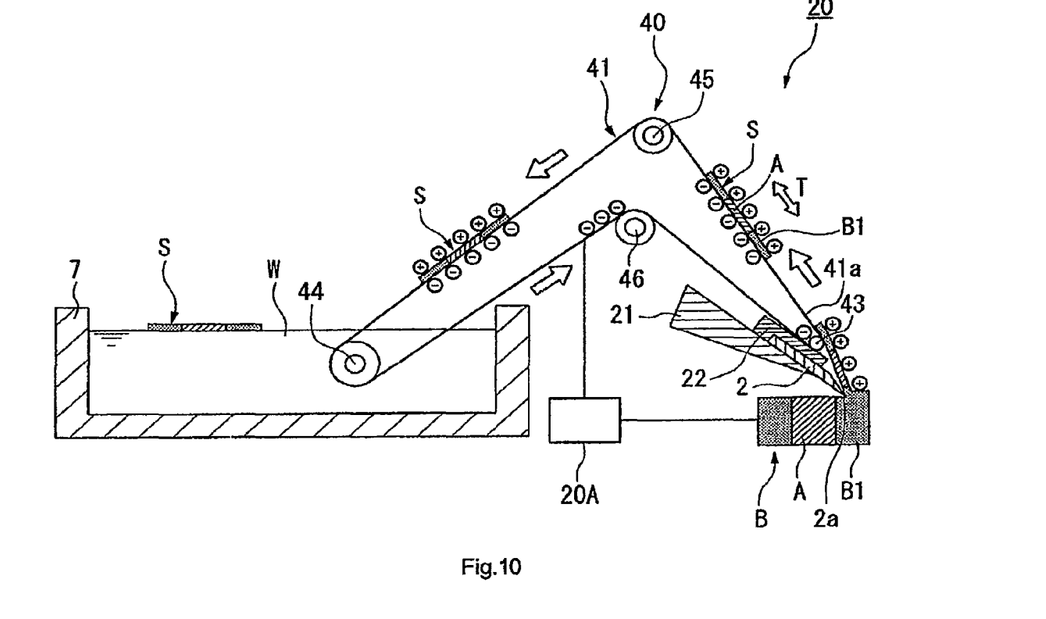
FIG. 10 shows a partial side view depicting a modification of a thin section preparing apparatus according to the invention.

For example, in the embodiments, the endless belt 41 containing a certain amount of a predetermined fluid W is used as the endless belt 41. However, the carrying body is not limited thereto. For example, as shown in FIG. 10, in a thin section preparing apparatus 20 having a charging mechanism 20A that charges electric charges of different polarities to an embedded block B and to an endless belt 41, the thin section S and the endless belt 41 may be brought into intimate contact with each other by using static electricity. In addition, although the adhesion to the thin section S is degraded, a simple endless belt may be used as the carrying body.

In addition, in the embodiments, in the cutting step S1, the embedded block B is moved along the approaching and separating direction X in order to relatively move the embedded block B and the cutter 2 in the approaching and separating direction X. However, the scheme is not limited thereto. For example, such a scheme may be possible that the position of the embedded block B is fixed to move the cutter 2 along the approaching and separating direction X. In addition, both of the embedded block B and the cutter may be moved along the approaching and separating direction X. However, at this time, it is necessary that the carrying mechanism 40 follows the operation of the cutter 2.

In addition, in the embodiments, in the cutting step S1, the endless belt 41 is moved along the moving direction Y in order to relatively move the embedded block B and the endless belt 41 in the moving direction Y. However, the scheme is not limited thereto. For example, such a scheme may be possible that the position of the endless belt 41 is fixed to move the embedded block B along the moving direction Y. In addition, both of the embedded block B and the endless belt 41 may be moved along the moving direction Y.

In addition, in the embodiments, in the cutting step S1, the sliding mechanism 50 is operated at the same time at which the operation of the X-stage 30 is started. However, the scheme is not limited thereto.

In other words, it is sufficient that the sliding mechanism 50 is in operation in placing the thin section S sliced off from the embedded block B onto the top surface 41a of the endless belt 41. For example, such a method may be used that in the cutting step S1, the time necessary from the start of the operation of the X-stage 30 to the start of the sliced thin section S being turned on the endless belt 41 is stored in advance and the operation of the sliding mechanism 50 is started based on this time. In addition, such a method may be used that a detecting unit is provided at a contact point between the thin section S and the endless belt 41, which detects the thin section S being turned on and sends a signal, and the operation of the sliding mechanism 50 is started based on the signal sent from the detecting unit.

What is claimed is:

1. A thin section preparing method of slicing an embedded block having a biological sample embedded therein by a cutter to prepare a thin section and carrying the thin section to a subsequent process step, the method comprising the steps of:

cutting wherein the embedded block and the cutter are relatively moved along an approaching and separating direction in which the embedded block and the cutter approach and separate from each other, and the thin section is sliced off from the embedded block at a predetermined pull angle; and carrying wherein the thin section sliced in the cutting step is placed on a top surface of a carrying body that is arranged as one end side thereof is near a nose of the cutter and is moved in a transport direction, the transport direction being substantially in parallel with a nose direction, and the thin section is carried from one end side of the carrying body toward the other end side thereof along the transport direction, wherein in conducting the cutting step and the carrying step, control is conducted in such a way that the embedded block and the carrying body are relatively moved at a predetermined rate of travel in a moving direction which is substantially vertical to the transport direction, the carrying body is moved at a predetermined transport velocity, and a combined velocity vector that combines a relative travel velocity vector of the embedded block to the carrying body with a transport velocity vector of the carrying body becomes nearly equal to a block velocity vector of the embedded block with respect to the cutter along the approaching and separating direction.

2. The thin section preparing method according to claim 1, wherein the carrying body contains a certain amount of a predetermined fluid, and
in conducting the carrying step, surface tension of the fluid is used to carry the thin section while the thin section is brought into intimate contact with the carrying body.

3. The thin section preparing method according to claim 1, wherein an endless belt is used as the carrying body.

4. The thin section preparing method according to claim 1, wherein in conducting the cutting step, the embedded block is moved along the approaching and separating direction, and the carrying body is moved along the nose direction.

5. A thin section preparing method of slicing an embedded block having a biological sample embedded therein by a cutter to prepare a thin section and carrying the thin section to a subsequent process step, the method comprising the steps of:
cutting wherein the embedded block and the cutter are relatively moved along an approaching and separating direction in which the embedded block and the cutter approach and separate from each other, and the thin section is sliced off from the embedded block at a predetermined pull angle; and
carrying wherein the thin section sliced in the cutting step is placed on a top surface of a carrying body that is arranged as one end side thereof is near a nose of the cutter and is moved in a transport direction, the transport direction being substantially in parallel with a nose direction, and the thin section is carried from one end side of the carrying body toward the other end side thereof along the transport direction,
wherein in conducting the cutting step and the carrying step, control is conducted in such a way that the embedded block and the carrying body are relatively moved at a predetermined rate of travel in a moving direction which is substantially vertical to the transport direction, the carrying body is moved at a predetermined transport velocity, and that a moving velocity of the embedded block in the nose direction is controlled based on the predetermined transport velocity of the carrying body along the transport direction and a block velocity of the embedded block with respect to the cutter along the approaching and separating direction.

6. The thin section preparing method according to claim 5, wherein in conducting the cutting step and the carrying step, control is further conducted in such a way that a magnitude of a combined velocity vector that combines a relative travel velocity vector of the embedded block to the carrying body along the moving direction with a transport velocity vector of the carrying body becomes nearly equal to a magnitude of a block velocity vector of the embedded block with respect to the cutter along the approaching and separating direction.

7. A thin section preparing apparatus that slices an embedded block having a biological sample embedded therein to prepare a thin section, and carries the thin section to a subsequent process step, the apparatus comprising:
a cutter that slices the embedded block at a predetermined pull angle;
an approaching and separating mechanism that relatively moves the embedded block and the cutter along an approaching and separating direction in which the embedded block and the cutter approach and separate from each other, and slices off the thin section from the embedded block;
a carrying mechanism that has:
a carrying body that is arranged as one end side thereof is near a nose of the cutter and the sliced thin section is placed on a top surface thereof; and
a moving unit that relatively moves the carrying body to the embedded block in a transport direction, the transport direction being substantially in parallel with a nose direction,
wherein the placed thin section is carried from one end side of the carrying body toward the other end side thereof along the transport direction;
a sliding mechanism that relatively moves the carrying body to the embedded block in a moving direction, the moving direction being substantially vertical to the transport direction; and
a control unit that controls rates of travel of the sliding mechanism and the moving unit in slicing off the thin section from the embedded block in such a way that a combined velocity vector that combines a transport velocity vector of the carrying body along the transport direction with a relative travel velocity vector of the embedded block to the carrying body along the moving direction becomes nearly equal to a block velocity vector of the embedded block with respect to the cutter along the approaching and separating direction.

8. The thin section preparing apparatus according to claim 7, wherein the carrying body contains a certain amount of a predetermined fluid.

9. The thin section preparing apparatus according to claim 7, wherein the carrying body is an endless belt.

10. The thin section preparing apparatus according to claim 7, wherein the approaching and separating mechanism has a guide rail extended along the approaching and separating direction and a stage movable along the guide rail as the stage holds the embedded block, and
the sliding mechanism has a slider unit that moves the carrying body along the moving direction.

11. A thin section preparing apparatus that slices an embedded block having a biological sample embedded therein to prepare a thin section, and carries the thin section to a subsequent process step, the apparatus comprising:
a cutter that slices the embedded block at a predetermined pull angle;
an approaching and separating mechanism that relatively moves the embedded block and the cutter along an approaching and separating direction in which the embedded block and the cutter approach and separate from each other, and slices off the thin section from the embedded block;
a carrying mechanism that has:
a carrying body that is arranged as one end side thereof is near a nose of the cutter and the sliced thin section is placed on a top surface thereof; and
a moving unit that relatively moves the carrying body to the embedded block in a transport direction, the transport direction being substantially in parallel with a nose direction,
wherein the placed thin section is carried from one end side of the carrying body toward the other end side thereof along the transport direction;
a sliding mechanism that relatively moves the carrying body to the embedded block in a moving direction, the moving direction being substantially vertical to the transport direction; and a control unit that controls rates of travel of the sliding mechanism and the moving unit in slicing off the thin section from the embedded block in such a way that a moving velocity of the thin section sliced off from the embedded block in the nose direction is controlled based on a transport velocity of the carrying body along the transport direction and a block velocity of the embedded block with respect to the cutter along the approaching and separating direction.

12. The thin section preparing apparatus according to claim 11, wherein the control unit further controls rates of travel of the sliding mechanism and the moving unit in slicing off the thin section from the embedded block in such a way that a magnitude of a combined velocity vector that combines a transport velocity vector of the carrying body along the transport direction with a relative travel velocity vector of the embedded block to the carrying body along the moving direction becomes nearly equal to a magnitude of a block velocity vector of the embedded block with respect to the cutter along the approaching and separating direction.

* * * * *